(12) United States Patent
Shouche et al.

(10) Patent No.: US 11,078,156 B2
(45) Date of Patent: Aug. 3, 2021

(54) AMMOXIDATION REACTOR CONTROL

(71) Applicant: INEOS EUROPE AG, Rolle (CH)

(72) Inventors: Manoj Shrikant Shouche, Pearland, TX (US); Timothy Robert McDonel, Elburn, IL (US); Jay Robert Couch, Naperville, IL (US)

(73) Assignee: INEOS EUROPE AG, Rolle (CH)

( * ) Notice: Subject to any disclaimer, the term of this patent is extended or adjusted under 35 U.S.C. 154(b) by 0 days.

(21) Appl. No.: 16/301,882

(22) PCT Filed: May 4, 2017

(86) PCT No.: PCT/US2017/030961
§ 371 (c)(1),
(2) Date: Nov. 15, 2018

(87) PCT Pub. No.: WO2017/205021
PCT Pub. Date: Nov. 30, 2017

(65) Prior Publication Data
US 2019/0152898 A1    May 23, 2019

(30) Foreign Application Priority Data

May 24, 2016 (CN) .......................... 201610346926.5

(51) Int. Cl.
*C07C 253/26* (2006.01)
*C07C 253/24* (2006.01)
*C07C 255/08* (2006.01)
*B01J 8/18* (2006.01)

(52) U.S. Cl.
CPC ........... *C07C 253/26* (2013.01); *B01J 8/1809* (2013.01); *B01J 8/1827* (2013.01); *B01J 8/1836* (2013.01); *C07C 253/24* (2013.01); *B01J 2208/00141* (2013.01); *B01J 2208/00548* (2013.01); *B01J 2208/00628* (2013.01)

(58) Field of Classification Search
CPC ..... C07C 253/26; B01J 8/1809; B01J 8/1827; B01J 8/1836; B01J 2208/00548; B01J 2208/00141; B01J 2208/00628
USPC ......................................................... 558/320
See application file for complete search history.

(56) References Cited

FOREIGN PATENT DOCUMENTS

| CN | 103097014 | 5/2013 | |
|---|---|---|---|
| CN | 104190331 | 12/2014 | |
| CN | 204841589 | 12/2015 | |
| JP | 9-208550 | 8/1997 | |
| JP | 10-139749 | 5/1998 | |
| JP | 2001-122805 | 5/2001 | |
| JP | 2008080219 | 4/2008 | |
| WO | 2016036517 | 3/2016 | |
| WO | WO-2016036517 A1 * | 3/2016 | ............ B01J 8/1809 |
| WO | WO-2016144664 A2 * | 9/2016 | ........... C07C 253/24 |

OTHER PUBLICATIONS

International Searching Authority, International Search Report and Written Opinion issued in PCT/US2017/030961, dated Jul. 17, 2017, 9 pages.
International Bureau, International Preliminary Report on Patentability issued in PCT/US2017/030961, dated Nov. 27, 2018, 6 pages.

* cited by examiner

*Primary Examiner* — Joseph R Kosack
*Assistant Examiner* — Sagar Patel
(74) *Attorney, Agent, or Firm* — Ineos Europe AG

(57) ABSTRACT

A process is provided for control of an ammoxidation reactor. More specifically, the process includes controlling an amount of oxygen added to the reactor, steam temperature and linear velocity to minimize reactor temperature deviations.

23 Claims, 2 Drawing Sheets

AMMOXIDATION REACTOR CONTROL

A process is provided for control of an ammoxidation reactor. More specifically, the process includes controlling an amount of oxygen added to the reactor, steam temperature and linear velocity to minimize reactor temperature deviations.

BACKGROUND

Acrylonitrile is manufactured by an ammoxidation process where air, ammonia, and propylene are reacted in the presence of a catalyst in a fluidized bed reactor. This is an exothermic reaction, and the heat generated is removed by circulating water or steam through a set of cooling coils that remove the heat to generate steam or superheated steam. The reactor temperature and reactor linear velocity are key variables that need to be controlled to get the desired acrylonitrile yield. The reactor temperature is influenced by the amount of propylene added to the reactor, reactor pressure, the super heat steam temperature, and the number of cooling coils that are being used. The linear velocity is influenced by the amount of propylene, ammonia, and air added, and the reactor pressure. Cooling coil changes are very common in the acrylonitrile reactor. Coil changes are typically brought about by the process board operators during rate changes, or during the coil swapping process a process that takes out coils that have been in service for sometime, and replaces them with fresh coils that have better heat transfer capability.

It is desired to run the acrylonitrile reactors at the maximum possible linear velocity and at a fixed reactor temperature to get the best acrylonitrile yield. The main challenge in achieving this objective comes from the fact that the cooling coils for a given reactor have different cooling capacity, based on the number of passes they have. Thus, the temperature response varies depending on the type of coil that is added in or removed from service in the reactor. Traditional control schemes try to independently control the linear velocity and the reactor temperature, and usually take control action in a reactive manner, especially during coil changes inside the reactor. This invariably increases the response time of the controller, and takes a long time for the temperature to settle down after coil changes. A control scheme thus has to take into account the interaction between the key variables, and take preemptive control action during coil changes.

SUMMARY

An ammoxidation process provides for maximum reactor linear velocity and minimum deviations in reactor temperature. Increased linear velocity and minimal deviations in reactor temperature result in improved reactor efficiencies.

An ammoxidation process includes introducing a flow of a reactant stream into an ammoxidation reactor. The reactant stream includes ammonia, an oxygen containing gas, a hydrocarbon selected from the group consisting of propane, propylene, isobutene, isobutylene and mixtures thereof. The process includes providing steam to coils disposed in the ammoxidation reactor to provide a reactor operating temperature of about 350° C. to about 480° C. The process further includes controlling an amount of oxygen added to the reactor and the steam temperature to maintain a superficial reactor linear velocity.

In another aspect, an ammoxidation process includes introducing a flow of a reactant stream into an ammoxidation reactor. The reactant stream includes ammonia, an oxygen containing gas, a hydrocarbon selected from the group consisting of propane, propylene, isobutene, isobutylene and mixtures thereof. The process includes providing steam to coils disposed in the ammoxidation reactor to provide a reactor operating temperature of about 350° C. to about 480° C. The process further includes controlling an amount of oxygen added to the reactor and the steam temperature to maintain a superficial reactor linear velocity within about 95% of a target superficial reactor linear velocity and within about 95% of a target reactor temperature.

An ammoxidation process introducing a flow of a reactant stream into an ammoxidation reactor. The reactant stream includes ammonia, propylene and oxygen containing gas. The process includes providing superheated steam to superheat coils disposed in the ammoxidation reactor. In one aspect, a set of manipulated variables includes reactor oxygen flow, superheated steam temperature, absorber pressure and amount of lean water to an absorber and the set of controlled variable includes a reactor linear velocity and a reactor temperature. Controlling at least one set of controlled variables includes controlling an amount of oxygen added to the reactor and the superheated steam temperature.

BRIEF DESCRIPTION OF FIGURES

The above and other aspects, features and advantages of several aspects of the process will be more apparent from the following figures.

Figure 1:
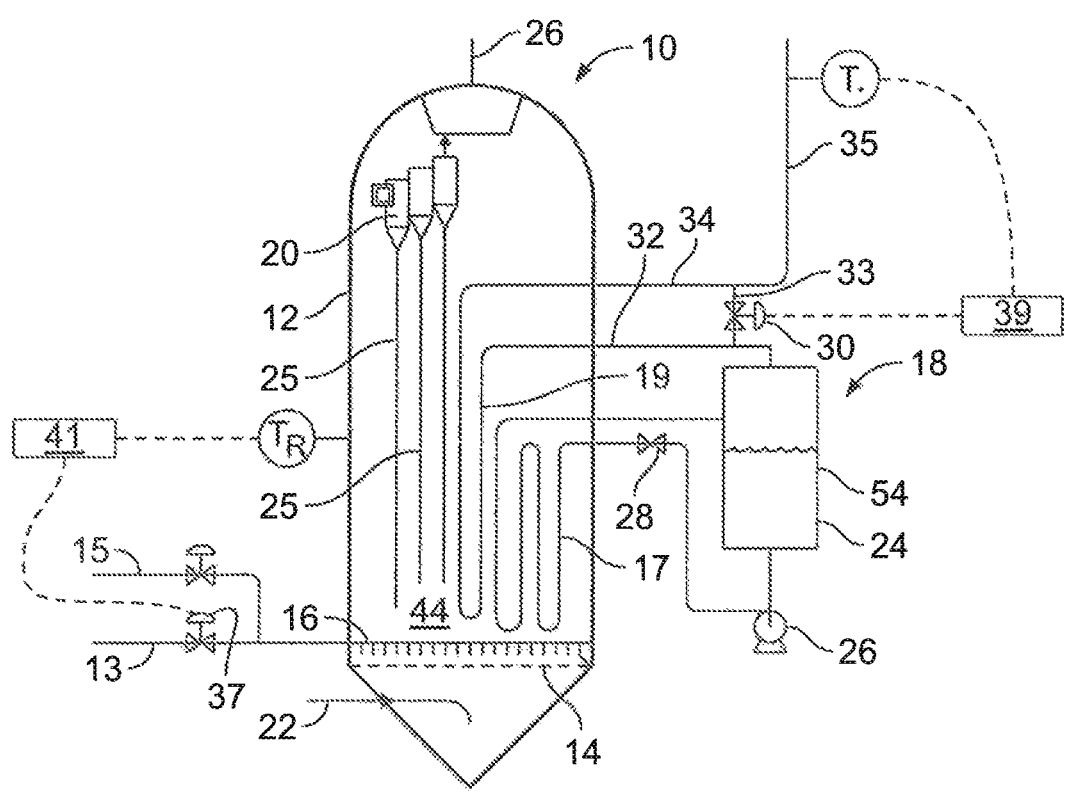
FIG. 1 illustrates ammoxidation process equipment.

Corresponding reference characters indicate corresponding components throughout the views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects. Also, common but well-understood elements that are useful or necessary in a commercially feasible aspect are often not depicted in order to facilitate a less obstructed view of these various aspects.

DETAILED DESCRIPTION

The following description is not to be taken in a limiting sense, but is made merely for the purpose of describing the general principles of exemplary embodiments. The scope of the invention should be determined with reference to the claims.

Ammoxidation Reactor

FIG. 1 illustrates a typical ammoxidation (acrylonitrile) reactor used. As shown, reactor 10 includes reactor shell 12, air grid 14, feed sparger 16, a cooling system generally indicated at 18 including saturated cooling coils 17 and superheat cooling coils 19, and cyclones 20. While FIG. 1 shows saturated cooling coils 17 and superheat cooling coils 19 being located on one side of reactor 10 and cyclones 20 being located on the other side, it will be understood that in actual practice these structures are positioned uniformly throughout the reactor. During normal operation, the process includes introducing a flow of reactant stream that includes ammonia, an oxygen containing gas, and a hydrocarbon selected from the group consisting of propane, propylene, isobutene, isobutylene and mixtures thereof. In one aspect, process air is charged into reactor 10 through air inlet 22, while a mixture of propylene obtained from propylene supply line 13 and ammonia obtained from ammonia supply line 15 is charged into reactor 10 through feed sparger 16. The flow rates of both are high enough to fluidize a bed 44 of ammoxidation catalyst in the reactor interior, where the catalytic ammoxidation of the propylene and ammonia to acrylonitrile occurs. A flowrate of propylene to the ammoxidation reactor is effective for providing a ratio of oxygen to propylene of about 2 to about 2.1 and a ratio of ammonia to propylene of about 1 to about 1.5. Ammonia is controlled by an $NH_3/C_3$ controller.

Product gases produced by the reaction exit reactor 10 through reactor effluent outlet 26. Before doing so, they pass through cyclones 20, which remove any ammoxidation catalyst these gases may have entrained for return to catalyst bed 44 through diplegs 25. Ammoxidation is highly exothermic, and so cooling system 18 is used to withdraw excess heat and thereby keep the reaction temperature at an appropriate level.

As further illustrated in FIG. 1, in addition to saturated cooling coils 17 and superheat cooling coils 19, cooling system 18 also includes steam drum 24, recirculating pump 26, shut-off valve 28 and steam control valve 30. The lower portion of steam drum 24 is filled with saturated liquid cooling water maintained at an elevated pressure and elevated temperature such as about 255° C. at about 4.2 mPaG. The upper portion of steam drum 24 is filled with saturated steam in equilibrium with this liquid cooling water. As is well understood in the art, water exists as a liquid at these elevated temperatures because it is also under greater than one atmosphere of pressure.

The primary way cooling system 18 removes heat from the interior of reactor 10 is by the recirculation of liquid cooling water from the lower portion of steam drum 24 through cooling coils 17. For this purpose, recirculation pump 26 is arranged to pump liquid cooling water from the bottom of steam drum 24 through shut-off valve 28 and then through cooling coil 17. In cooling coil 17, some liquid vaporizes to steam and cooling water and steam produced is returned to steam drum 24. Since the saturated cooling water fed to cooling coil 17 is composed of 100% liquid water, cooling coil 17 is typically referred to as a "saturated" cooling coil.

In actual practice, the flowrate of cooling water through saturated cooling coil 17 is selected so that a predetermined proportion of this cooling water, typically about 15% for example, is converted to steam. Accordingly, as shown in FIG. 1, the heated cooling water produced in saturated cooling coil 17 is returned to an upper portion of steam drum 24, so that the vaporous fraction of this cooling water stream can remain in the upper portion of the steam drum while the liquid portion of this cooling water stream can fall to the lower portion of the steam drum for mixing with the liquid cooling water already there. The steam drum 24 may include make-up water conduit 54.

In many designs, shut-off valve 28 is a simple on-off valve as opposed to a control valve capable of fine control of fluid flowrate. This is because other means are typically used for fine control of the reaction temperature inside the acrylonitrile reactor, and so a more complicated and expensive control valve is unnecessary. Also it is not desirable to convert to much of the liquid water into vapor inside the cooling coil as this can result in negative consequences such as erosion of the inside of the cooling coil pipe or scaling.

Each individual shut-off valve 28 on each individual coil is the only valve controlling whether or not cooling water flows through a particular saturated cooling coil 17. That is to say, saturated cooling coil 17 is constructed without any additional valve or other flow control device for controlling the flow of cooling water through saturated cooling coil 17. This is because such an additional valve is unnecessary to achieve the desired operation and control of the cooling coils in the manner described here. In addition, eliminating a valve on the outlet also eliminates the need for a safety valve, which would otherwise be necessary if such an outlet valve were used. Thus, the total flow through all of the cooling coils in service (that is for the saturated cooling coil 17 which have their valve open) is set by a discharge flow rate from pump 26.

In addition to saturated cooling coils 17, cooling system 18 also uses superheat cooling coils 19 for removing heat from the interior of acrylonitrile reactor 10. Superheat cooling coils 19 differ from saturated cooling coils 17 in that superheat cooling coils 19 are connected by means of steam inlet header 32 to an upper portion of steam drum 24 so that the feed to these cooling coils is superheated steam rather than saturated steam. The steam entering superheat cooling coil 19 is at a saturation temperature corresponding to the steam drum pressure. The steam drum pressure increases as it flows through superheat cooling coil 19 and thus becomes superheated. Accordingly, cooling coils 19 are typically referred to as "superheat cooling coils." In this aspect, the process includes providing the superheat steam at a temperature of about 350° C. to about 480° C., in another aspect, about 355° C. to about 400° C., in another aspect, about 360° C. to about 390° C., and in another aspect, about 370° C. to about 380° C.

An important function of superheat cooling coils 19 is to raise the temperature of steam produced in coils 19 so as to provide superheated steam for driving the steam turbines used in other parts of the acrylonitrile plant as liquid droplets in wet steam may damage turbine internals. For this purpose, the superheated steam passing out of superheat cooling coils 19 is typically discharged through steam outlet header 34 to steam supply conduit 35 for transfer directly to these steam turbines.

Common practice in many acrylonitrile plants includes connecting steam inlet header 32 and steam outlet header 34 with bypass line 33 so that the temperature of the steam passing into steam supply conduit 35 can be controlled by adjusting the amount of steam supplied to this conduit directly from steam drum 24. Because the temperature of the steam in steam drum 24 is necessarily lower than the temperature of the superheated steam passing out of superheat cooling coil 19, increasing the flowrate of steam passing through bypass line 33 necessarily lowers the temperature of the steam reaching steam supply conduit 35. So, it is also customary in most commercial acrylonitrile plants also to include steam control valve 30 in bypass passageway 33, whose operation is controlled by controller 39 in response to the measured temperature $T_1$ of the steam in steam supply conduit 35. Control valve 30 is then operated to maintain the measured temperature $T_1$ of the steam in steam supply conduit 35 at a constant temperature somewhere between about 340 to 385° C.

In order to keep an acrylonitrile reactor operating in peak condition, it is desirable to maintain its operating temperature within a target temperature range of about 200 to about 480° C., in another aspect, about 215 to about 440° C., and in another aspect, about 215 to about 230° C., when modern molybdenum based ammoxidation catalysts are used. In this aspect, it is more desirable to maintain the reactor temperature as close as possible to a single control point temperature rather than to allow the operating temperature to drift up and down within a range of temperatures. Although control of reaction temperature can be carried out by adding to or subtracting from the number of cooling coils in active service, this approach does not provide precise temperature control. Rather, the addition and subtraction of cooling coils alone does not necessarily achieve the precise reactor operating temperature.

Accordingly, precise temperature control of acrylonitrile reactor 10 is commonly done by increasing and decreasing the flowrate of propylene supplied to the acrylonitrile reactor in response to the measured temperature $T_R$ of the ammoxidation reaction occurring inside the reactor. For this purpose, as illustrated in FIG. 1, propylene control valve 37 in propylene supply line 13 and controller 41 are provided to control the flow of propylene into acrylonitrile reactor 10 in response to the measured ammoxidation reaction temperature, $T_R$. Thus, a certain number of cooling coils are put into service to provide reactor temperature control within a desired temperature range, and a propylene feed rate is adjusted up or down to achieve a more precise temperature adjustment.

In one aspect, the process provides improved temperature control and reduced reactor temperature deviations during changes in heat transfer areas of coil. In this aspect, reactor temperature deviations are maintained at about 10° C. or less during changes in heat transfer area of the coils, in another aspect, about 6° C. or less, in another aspect, about 5° C. or less, and in another aspect, about 3° C. or less.

Every reactor may have a different target temperature within the ranges described herein. In one aspect, an amount of the oxygen added to the reactor and the steam temperature are controlled to maintain a reactor temperature within about 95% of a target reactor temperature, and in another aspect, within about 98% of a target reactor temperature.

In another aspect, a total available superheat coil area per reactor cross sectional area ($ft^2/ft^2$) is about 1 to about 7, in another aspect, about 2 to about 6, and in another aspect, about 3 to about 5. The superheat coil area ($ft^2$) per heat removed by the superheat coils (Kcal) per metric ton of acrylonitrile produced is about 275,000 to about 475,000, in another aspect, about 300,000 to about 400,000, and in another aspect, 325,000 to about 375,000.

In another aspect, a total available saturated coil area per reactor cross sectional area ($ft^2/ft^2$) is about 8 to about 18, in another aspect, about 8 to about 15, and in another aspect, about 10 to about 13. The saturated coil area ($ft^2$) per heat removed by the saturated coils (Kcal) per metric ton of acrylonitrile produced is about 2,375,000 to about 2,900,000, in another aspect, about 2,400,000 to about 2,800,000, and in another aspect, about 2,500,00 to about 2,700,000.

In an aspect, the process includes operating or reacting in a reactor a hydrocarbon, wherein the effluent flow has a linear velocity of about 0.5 to about 1.5 m/sec, in another aspect, about 0.7 to about 1.0 m/sec, in another aspect, about 0.75 to about 0.8 in/sec, and in another aspect, about 0.75 to about 0.77 in/sec (based on effluent volumetric flow and reactor cross-sectional area ("CSA") excluding cooling coils and dip legs area, i.e., ~90% of open CSA). It has been found that it is possible to design and operate the reactor system using this velocity whilst also achieving good fluidization/catalyst performance and reasonable catalyst entrainment/catalyst losses from cyclones, such that velocities may be maintained in about this range to the extent possible as reactor capacity is increased. In an embodiment, the reactor may be operated to maintain a top pressure of about 0.25 to about 0.5 kg/cm², and in another aspect, about 0.2 to about 0.45 kg/cm². In another aspect, an amount of the oxygen added to the reactor and the steam temperature are controlled to maintain a superficial reactor linear velocity within about 95% of a target superficial reactor linear velocity, and in another aspect, within about 98% of a target superficial reactor linear velocity.

In one aspect, a ratio of cyclone inlet velocity in meters/second to a reactor effluent velocity in meters/second is 20 or greater, in another aspect, about 20 to about 30, in another aspect, about 22 to about 25, in another aspect, about 23 to about 26, and in another aspect, about 27 to about 29.

In another aspect, the process includes controlling reactor top pressure at about 3.8 psig to about 5.0 psig, in another aspect, 4.0 psig to about 5.0 psig, and in another aspect, about 4.0 to about 4.5 psig.

Figure 2:
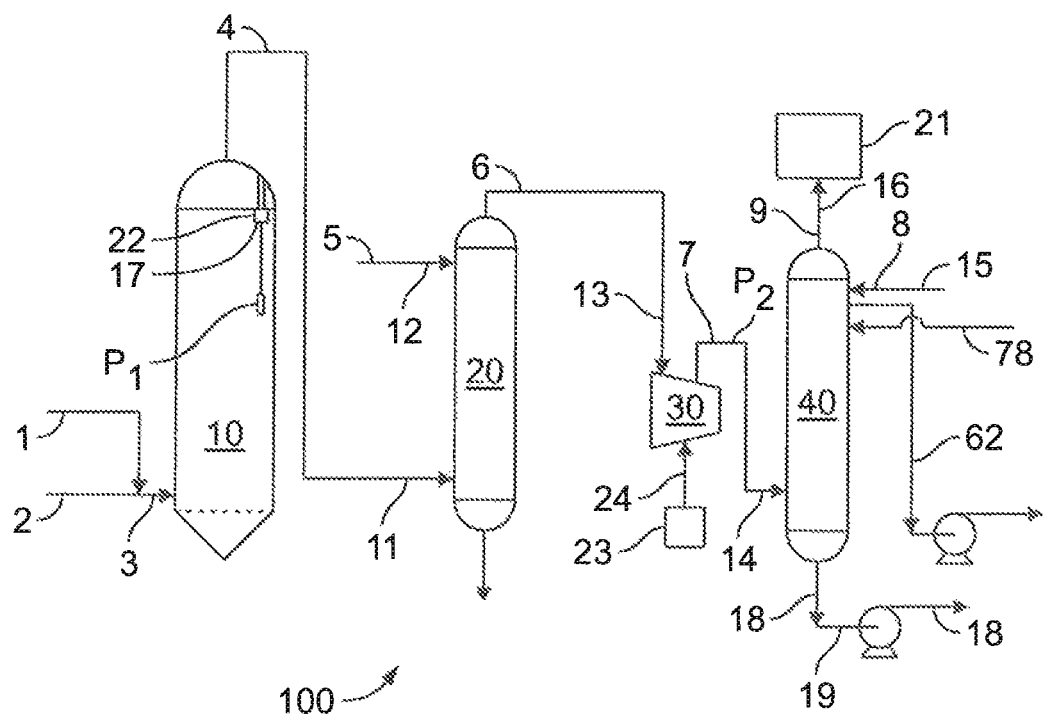
FIG. 2 illustrates an ammoxidation process.

FIG. 2 is a schematic flow diagram of an embodiment in accordance with aspects of the disclosure as applied to the manufacture of acrylonitrile. Referring to the figure, an apparatus 100 comprises reactor 10, quench vessel 20, effluent compressor 30, and absorber 40. Ammonia in stream 1 and hydrocarbon (HC) feed in stream 2 may be fed as combined stream 3 to reactor 10. HC feed stream 2 may comprise a hydrocarbon selected from the group consisting of propane, propylene and isobutylene, and combinations thereof. A catalyst (not shown in FIG. 2) may be present in reactor 10. Oxygen containing gas may be fed to reactor 10. For example, air may be compressed by an air compressor (not shown in FIG. 2) and fed to reactor 10.

Acrylonitrile is produced in reactor 10 from the reaction of the hydrocarbon, ammonia, and oxygen in the presence of a catalyst in reactor 10. Reactor 10 may be run at reactor or first pressure P1, wherein the first pressure may be characterized as the pressure at inlet 17, such as a first-stage inlet of cyclone 22. In accordance with the disclosure, cyclone 22 may be the first cyclone of a multi-stage cyclone system that may be configured to convey a stream comprising acrylonitrile to a plenum (not shown in FIG. 1). The stream comprising acrylonitrile may exit the plenum and out of a top portion of reactor 10 as reactor effluent stream 4. In an aspect, cyclone 22 may be configured to separate catalyst that may be entrained in the stream comprising acrylonitrile that enters inlet 17, and return the separated catalyst back to the catalyst bed in reactor 10 through a catalyst return dip leg (not shown in FIG. 1). Reactor effluent stream 4 comprising acrylonitrile produced in reactor 10 may be conveyed through line 11 to quench vessel 20. In this aspect, the first pressure is about 140 kPa or less, in another aspect about 135 kPa or less, in another aspect about 130 kPa or less, in another aspect about 125 kPa or less, in another aspect, about 101 kPa to about 140 kPa, in another aspect, about 110 kPa to about 1400 kPa, in another aspect, about 125 kPa to about 145 kPa, in another aspect, about 120 kPa to about 140 kPa, in another aspect, about 130 kPa to about 140 kPa, in another aspect, about 125 kPa to about 140 kPa, in another aspect, about 125 kPa to about 135 kPa, in another aspect, about 120 kPa to about 137 kPa, and in another aspect, about 115 kPa to about 125 kPa.

In quench vessel 20, reactor effluent stream 4 may be cooled by contact with quench aqueous stream 5 entering quench vessel 20 via line 12. Quench aqueous stream 5 may comprise an acid in addition to water. The cooled reactor effluent comprising acrylonitrile (including co-products such as acetonitrile, hydrogen cyanide and impurities) may then be conveyed as quenched stream 6 to effluent compressor 30 via line 13.

Quenched stream 6 may be compressed by effluent compressor 30, and exit effluent compressor 30 as compressor effluent stream 7. Compressor effluent stream 7 may have a second or compressed pressure P2. Compressor effluent stream 7 may be conveyed to a lower portion of absorber 40 via line 14. In absorber 40, acrylonitrile may be absorbed in a second or absorber aqueous stream 8 that enters an upper portion of absorber 40 via line 15. The aqueous stream or rich water stream 18 that include acrylonitrile and other co-products may then be transported from absorber 40 via line 19 a recovery column. (not shown in FIG. 2) for further product purification.

The non-absorbed effluent 9 exits from the top of absorber column 40 through pipe 16. Non-absorbed effluent 9 may comprise off-gases, which can be burned in absorber off-gas incinerator (AOGI) or absorber off-gas oxidizer (AOGO).

In an aspect, effluent compressor 30 functions by pulling quenched stream 6 through line 13. Effluent compressor 30 may compress quenched stream 6 so that it exits effluent compressor 30 as compressed effluent compressor stream 7 that has a higher pressure (second pressure) than the reactor pressure (first pressure). In an aspect, the pressure in line 14 of compressed effluent compressor stream 7 is about 2 to about 11.5 times greater than the operation pressure of reactor 10, in another aspect, about 2 to about 12.5 times, in another aspect, about 2.5 to about 10, in another aspect, about 2.5 to about 8, in another aspect, about 2.5 to about 5, in another aspect, about 2.5 to about 4, in another aspect, about 2.5 to about 3.2, in another aspect, about 2 to about 3.5, in another aspect, about 2 to about 3, in another aspect, about 3 to about 11.25, in another aspect, about 5 to about 11.25, and in another aspect, about 7 to about 11.25 (all based on an absolute comparison). In an aspect, the second pressure (absolute) is about 300 to about 500 kPa, in another aspect, about 340 kPa to about 415 kPa, in another aspect, about 350 kPa to about 400 kPa, in another aspect, about 250 kPa to about 500 kPa, in another aspect, about 200 kPa to about 400 kPa, in another aspect, about 250 kPa to about 350 kPa, in another aspect, about 300 kPa to about 450 kPa, and in another aspect, about 360 kPa to about 380 kPa.

In an aspect, the second pressure is such that the absorber may be operated with a flow rate of aqueous stream 8 of about 15 to about 20 kg/kg of acrylonitrile final product produced when aqueous stream 8 is uncooled or unrefrigerated and/or is 4 to about 45° C. and wherein the absorber rich water stream contains about 5 weight percent or more organics, in another aspect, about 6 weight percent or more organics, and in another aspect, about 7 weight percent or more organics. In another aspect, the flow rate of aqueous stream 8 may be about 15 to about 19 kg/kg of acrylonitrile, in another aspect, about 15 to about 18 kg/kg of acrylonitrile, and in another aspect, about 16 to about 18 kg/kg of acrylonitrile. In another aspect, the uncooled or unrefrigerated aqueous stream is about 20 to about 45° C., in another aspect, about 25 to about 40° C., in another aspect, about 25 to about 35° C., and in another aspect, about 25 to about 30° C.

A cooling system (not shown in FIG. 2) may be located at or downstream of compressor 30, wherein the cooling system is configured to cool compressed effluent compressor stream 7 to a predetermined temperature, e.g., about 105° F. (about 40.5° C.) prior to entering absorber 40.

In an aspect, absorber 40 may include forty to sixty (40-60) trays. In an aspect, absorber 40 may include fifty (50) trays. Compressed effluent compressor stream 7 may enter absorber 40 below the bottom tray of the absorber. In an aspect, absorber 40 may be operated with variable flow rates of refrigerated water in second aqueous stream 8, including zero amount of refrigerated water.

In an aspect, absorber 40 may be operated at pressure that is higher than the pressure in an absorber in a conventional process. By operating absorber 40 at this higher pressure, the absorber may be operated more efficiently than an absorber in a conventional process. Due to the higher absorber efficiency achieved in the process of the present disclosure, the same recovery of acrylonitrile in rich water stream 18 may be achieved as in a conventional process, but less water is required to absorb acrylonitrile in the absorber. In this aspect, rich water refers to water having about 5 weight percent or more organics, in another aspect, about 6 weight percent or more organics, and in another aspect, about 7 weight percent or more organics. In an aspect, the water used to absorb acrylonitrile in the absorber may be process or municipal water (e.g., having a temperature of about 4-45° C.). In this aspect, process or municipal water is more than about 95 weight percent water, in another aspect, about 97 weight percent or more water, in another aspect, about 99 weight percent or more water, and in another aspect, about 99.9 weight percent or more water. In an aspect, the temperature of second aqueous stream 8 may be in the range of about 4 to about 45° C., in another aspect, about 10 to about 43° C., and in another aspect, about 27 to about 32° C.

Advanced Process Control

A model predictive control (MPC), also known as advanced process control (APC), uses a process model to predict the behavior of a process into the future, and then implements an optimized control action to counter process deviation from a desired target. Along with controlling the process, MPC also tries to drive the process towards the most "economic" condition by moving the key process variables. One aspect of the present process includes an MPC to control the reactor temperature and the linear velocity. The process includes using MPC to achieve the maximum linear velocity possible for the reactor and a constant reactor temperature with minimum deviations during coil changes.

As used herein, the term "manipulated variable" refers to variables that are adjusted by the advanced process controller. The term "controlled variables" refers to variable that are kept by the advanced process controller at a predetermined value (set point) or within a predetermined range (set range). "Optimizing a variable" refers to maximizing or minimizing the variable and to maintaining the variable at a predetermined value.

One aspect of model predictive control is that future process behavior is predicted using a model and available measurements of the controlled variables. The controller outputs are calculated so as to optimize a performance index, which is a linear or quadratic function of the predicted errors and calculated future control moves. At each sampling instant, the control calculations are repeated and predictions updated based on current measurements. In this aspect, a suitable model is one that includes a set of empirical step-response models expressing the effects of a step-response of a manipulated variable on the controlled variables.

An optimum value for e parameter to be optimized can be obtained from a separate optimization step, or the variable to be optimized can be included in the performance function.

Before model predictive control can be applied, one determines first the effect of step changes of the manipulated variables on the variable to be optimized and on the controlled variables. This results in a set of step-response coefficients. This set of step-response coefficients forms the basis of the model predictive control of the process.

During normal operation, the predicted values of the controlled variables are regularly calculated for a number of future control moves. For these future control moves a performance index is calculated. The performance index includes two terms, a first term representing the sum over the future control moves of the predicted error for each control move and a second term representing the sum over the future control moves of the change in the manipulated variables for each control move. For each controlled variable, the predicted error is the difference between the predicted value of the controlled variable and a reference value of the controlled variable. The predicted errors are multiplied with a weighting factor, and the changes in the manipulated variables for a control move are multiplied with a move suppression factor. The performance index discussed here is linear.

Alternatively, the terms may be a sum of squared terms, in which case the performance index is quadratic. Moreover, constraints can be set on manipulated variables, changes in manipulated variables and on controlled variables. This results in a separate set of equations that are solved simultaneously with the minimization of the performance index.

Optimization can be done in two ways; one way is to optimize separately, outside the minimization of the performance index, and the second way is to optimize within the performance index.

When optimization is done separately, the variables to be optimized are included as controlled variables in the predicted error for each control move and the optimization gives a reference value for the controlled variables.

Alternatively, optimization is done within the calculation of the performance index, and this gives a third term in the performance index with an appropriate weighting factor. In this case, the reference values of the controlled variables are predetermined steady state values, which remain constant.

The performance index is minimized taking into account the constraints to give the values of the manipulated variables for the future control moves. However, only the next control move is executed. Then the calculation of the performance index for future control moves starts again.

The models with the step response coefficients and the equations required in model predictive control are part of a computer program that is executed in order to control the liquefaction process. A computer program loaded with such a program that can handle model predictive control is called an advanced process controller. Commercially available computer programs that may be utilized include for example, DMCplus® by Aspen Technology and Predict-Pro® by Emerson.

While the invention herein disclosed has been described by means of specific embodiments, examples and applications thereof, numerous modifications and variations could be made thereto by those skilled in the art without departing from the scope of the invention set forth in the claims.

What is claimed is:

1. An ammoxidation process comprising:
   introducing a flow of reactant stream into an ammoxidation reactor, wherein the reactant stream includes ammonia, an oxygen containing gas, a hydrocarbon selected from the group consisting of propane, propylene, isobutene, and isobutylene, or mixtures thereof;
   providing superheated steam to superheat coils disposed in the ammoxidation reactor to provide a reactor operating temperature of about 350° C. to about 480° C., wherein reactor temperature deviations are maintained at about 10° C. or less during changes in a heat transfer area of the superheat coils; and
   conveying a reactor effluent to an absorber, wherein the absorber has a pressure of about 35 psig to about 40 psig,
   wherein an amount of the oxygen added to the reactor and the steam temperature are controlled to maintain a superficial reactor linear velocity between about 0.5 m/s to 1.5 m/s,
   wherein a total available superheat coil area per reactor cross sectional area ($ft^2/ft^2$) is about 1 to about 7.

2. The process of claim 1 wherein the superficial reactor linear velocity is maintained between about 0.7 m/s to about 1.0 m/s.

3. The process of claim 2 wherein the superficial reactor linear velocity is maintained between about 0.75 m/s to about 0.80 m/s.

4. The process of claim 1 wherein the superheat steam is provided with a temperature of about 355° C. to about 400° C.

5. The process of claim 1 wherein a reactor top pressure is maintained at about 3.8 psig to about 5.0 psig.

6. The process of claim 1 wherein the superheat coil area ($ft^2$) per heat removed by the superheat coils (kcal) per metric ton of acrylonitrile produced is about 275,000 to about 475,000.

7. The process of claim 1 wherein the reactant stream includes propylene.

8. The process of claim 7 wherein a flowrate of propylene to the ammoxidation reactor is effective for providing a ratio of oxygen to propylene of about 2 to about 2.1 and a ratio of ammonia to propylene of about 1 to about 1.5.

9. An ammoxidation process comprising:
   introducing a flow of reactant stream into an ammoxidation reactor, wherein the reactant stream includes ammonia, an oxygen containing gas, a hydrocarbon selected from the group consisting of propane, propylene, isobutene, and isobutylene, or mixtures thereof; and
   providing steam to coils disposed in the ammoxidation reactor to provide a reactor operating temperature of about 350° C. to about 480° C., wherein reactor temperature deviations are maintained within about 98% of the reactor temperature during changes in a heat transfer area of the coils; and
   conveying a reactor effluent to an absorber, wherein the absorber has a pressure of about 35 psig to about 40 psig,
   wherein an amount of the oxygen added to the reactor and the steam temperature are controlled and a superficial reactor linear velocity is maintained within about 95% of a target superficial reactor linear velocity of between about 0.5 m/s to about 1.5 m/s and within about 95% of a target reactor temperature,
   wherein a total available superheat coil area per reactor cross sectional area ($ft^2/ft^2$) is about 1 to about 7.

10. The process of claim 9 wherein the superficial reactor linear velocity is maintained within about 98% of the target superficial reactor linear velocity.

11. The process of claim 9 wherein the steam is superheated steam and the coils are superheated coils.

12. The process of claim 11 wherein the superheat steam is provided with a temperature of about 355° C. to about 400° C.

13. The process of claim 9 wherein a reactor pressure is maintained at about 3.8 psig to about 5.0 psig.

14. The process of claim 9 wherein the superheat coil area (ft$^2$) per heat removed by the superheat coils (kcal) per metric ton of acrylonitrile produced is about 275,000 to about 475,000.

15. The process of claim 9 wherein the reactant stream includes propylene.

16. The process of claim 15 wherein a flowrate of propylene to the ammoxidation reactor is effective for providing a ratio of oxygen to propylene of about 2 to about 2.1 and a ratio of ammonia to propylene of about 1 to about 1.5.

17. An ammoxidation process comprising:
introducing a flow of reactant stream into an ammoxidation reactor, wherein the reactant stream includes ammonia, a hydrocarbon selected from the group consisting of propane, propylene, isobutene, and isobutylene, or mixtures thereof, and an oxygen containing gas;
providing superheated steam to superheat coils disposed in the ammoxidation reactor, wherein reactor temperature deviations are maintained at about 10° C. or less during changes in a heat transfer area of the superheat coils; and
conveying a reactor effluent to an absorber, wherein the absorber has a pressure of about 35 psig to about 40 psig,
wherein the process includes controlling superficial reactor linear velocity and reactor operating temperature based on model predictive control to determine simultaneous control actions for manipulated variables in order to optimize at least one set of parameters while controlling at least one set of controlled variables,
wherein the set of manipulated variables includes superheated steam temperature, absorber pressure and amount of lean water to an absorber and the set of controlled variable includes a reactor linear velocity and a reactor temperature,
wherein the process provides a superficial reactor linear velocity of about 0.5 m/s to about 1.5 m/s.

18. The process of claim 17 wherein the process provides a reactor linear velocity of about 0.7 m/s to about 1.0 m/s.

19. The process of claim 18 wherein the process provides a reactor linear velocity of about 0.75 m/s to about 080 m/s.

20. The process of claim 17 wherein the reactor pressure is maintained at about 3.8 psig to about 5.0 psig.

21. The process of claim 17 wherein reactor temperature deviations are maintained at about 5° C. or less during changes in a heat transfer area of the coils.

22. The process of claim 17 wherein the superheat steam has a temperature of about 355° C. to about 400° C.

23. The process of claim 17 wherein a flowrate of propylene to the ammoxidation reactor is effective for providing a ratio of oxygen to propylene of about 2 to about 2.1 and a ratio of ammonia to propylene of about 1 to about 1.5.

* * * * *